US010002232B2

(12) United States Patent
Hong et al.

(10) Patent No.: US 10,002,232 B2
(45) Date of Patent: Jun. 19, 2018

(54) BIOLOGICAL SAMPLE ANALYSIS SYSTEM AND METHOD

(71) Applicants: SAMSUNG SDS CO., LTD., Seoul (KR); SAMSUNG LIFE PUBLIC WELFARE FOUNDATION, Seoul (KR)

(72) Inventors: Yoo Jin Hong, Seoul (KR); Seong Hyeuk Nam, Seoul (KR); Yong Seok Lee, Seoul (KR); Sung Soo Kang, Seoul (KR); Chang Seok Ki, Seoul (KR)

(73) Assignees: SAMSUNG SDS CO., LTD., Seoul (KR); SAMSUNG LIFE PUBLIC WELFARE FOUNDATION., Seoul (KR)

( * ) Notice: Subject to any disclaimer, the term of this patent is extended or adjusted under 35 U.S.C. 154(b) by 792 days.

(21) Appl. No.: 14/290,965

(22) Filed: May 29, 2014

(65) Prior Publication Data

US 2015/0105263 A1 Apr. 16, 2015

(30) Foreign Application Priority Data

Oct. 11, 2013 (KR) .................. 10-2013-0121568

(51) Int. Cl.
*G01N 33/48* (2006.01)
*G06F 19/24* (2011.01)

(52) U.S. Cl.
CPC .................... *G06F 19/24* (2013.01)

(58) Field of Classification Search
None
See application file for complete search history.

*Primary Examiner* — Larry D Riggs, II
(74) *Attorney, Agent, or Firm* — Sughrue Mion, PLLC

(57) ABSTRACT

Disclosed are a biological sample analysis system and method for determining whether or not each of a plurality of biological samples has a test-target property using the plurality of biological samples and a plurality of pools generated by pooling samples. The system includes a determiner configured to determine whether or not there is a possibility of a determination of a false positive according to test values for the test-target property of the plurality of pools, an additional sample selector configured to select a minimum number of additional test-target samples on which an individual test of whether or not a sample has the test-target property will be carried out from among the plurality of samples when it is determined that there is the possibility of a determination of a false positive, and a test result determiner configured to determine whether or not each of the plurality of samples has the test-target property according to test results of the additional test-target samples.

12 Claims, 13 Drawing Sheets

FIG. 6

```
Input:     a graph G=(Vs, Vp, E)
           Vs: vertices representing each sample in positive pools
           Vp: vertices representing each positive pool
           E: edges between Vs and Vp if the pool represented as Vp
           contains the sample represented as Vs Output:    L, a set of Vs representing minimum number of the samples
           to run experiment function pickSampleForExperiment(G)
    L = empty
    Q = the set of all Vs in G
    R = the set of all Vp in G
    while Q is not empty
        // Select the Pool P
        u = vertex in R with the smallest # of neighbor vertices in Q
        remove u from R
        D = neighbor vertices of u in Q
        while D is not empty
        x = vertex in D
            // Skip the sample S
            remove x from D and Q
            if D is not empty
                // Select the sample S for individual test
                insert x to L
            end if
        end while
    end while
return L
end function
```

FIG. 8

```
Input:     a graph G=(Vs, Vp, E), an integer array valS, and
           an integer array valP
           Vs: vertices representing each sample in positive pools
           Vp: vertices representing each positive pool
           E: edges between Vs and Vp if the pool represented as Vp
           contains the sample represented as Vs
           valS: variant values for all Vs. If not known, null
           valP: pool values for all Vp
Output:    valS, variant values for all Vs or error message function calculateSampleValue(G)
    L = empty
    Q = the set of all Vs in G
    R = the set of all Vp in G
    for each vertex u in Q
        if valS[u] is not null
            D = neighbor vertices of u in R
            // Remove the value of the sample S
            remove u from Q
            for each vertex v in D
                // Adjust the value of the pool P
                valP[v] = valP[v] - valS[u]
            end for
        end if
    end for
    while Q is not empty
        u = vertex in R with a single neighbor vertex in Q
        v = neighbor vertex of u
        valS[v] = valP[u]
        remove u from R
        remove v from Q
        D = neighbor vertices of v in R
        for each vertex x in D
            // Get the value of the sample S from the value of the pool P
            valP[x] = valP[x] - valS[v]
        end for
    end while
    return valS
end function
```

BIOLOGICAL SAMPLE ANALYSIS SYSTEM AND METHOD

CROSS-REFERENCE TO RELATED APPLICATION

This application claims priority to and the benefit of Korean Patent Application No. 10-2013-0121568, filed on Oct. 11, 2013, the disclosure of which is incorporated herein by reference in its entirety.

BACKGROUND

1. Technical Field

The present disclosure relates to technology for analyzing a biological sample, and more particularly, to a biological sample analysis system and method.

2. Discussion of Related Art

In general, a sample of each test target is individually tested to examine whether or not a biological sample of the test target has a specific property as in an example of testing a blood sample to examine whether the blood sample has been infected with a specific virus or whether the blood sample has a specific mutation causing a disease. Therefore, when a large number of samples are tested, much time and cost are required for as many repetition tests as the number of samples.

The most basic method of carrying out the same test on a large number of samples is to individually carry out the test on each sample. At this time, cost for the test increases as much as the number of samples to be tested. For example, when a selective test is carried out for a disease with low incidence, most tested samples show negative results. To reduce cost for the test in this case, methods for testing several samples at a time have been proposed.

In one existing method for testing several samples at a time, a test is carried out on a sample obtained by mixing several samples at different ratios, and it is determined which one of the mixed samples has a specific property according to the intensity of a signal indicating the specific property in results of the test. However, as the number of samples to be tested at a time increases, this method requires a large amount of samples to be mixed. For example, to test 16 samples at a time, the samples are mixed at a ratio of $1:2:2^2:2^3 \ldots 2^{14}:2^{15}$. This case requires the last sample as much as $2^{15}$ (=32,768) times the first sample, and it is almost impossible to apply such a large amount of sample in practice.

There are US Unexamined Patent Application Publication Nos. 2010-0216666 (Aug. 26, 2010) and 2012-0185177 (Jul. 19, 2012) as the patent literature of the related art.

SUMMARY

Embodiments of the present disclosure are directed to providing a means for minimizing the number of times of a test for examining whether or not a plurality of biological samples have a specific property.

According to an aspect of the present disclosure, there is provided a biological sample analysis system for determining whether or not each of a plurality of biological samples constituting an n×m matrix has a test-target property using the plurality of biological samples and a plurality of pools generated by pooling samples of each row or column in the matrix, the system including: a determiner configured to determine whether or not there is a possibility of a determination of a false positive according to test values for the test-target property of the plurality of pools; an additional sample selector configured to select a minimum number of additional test-target samples on which an individual test of whether or not a sample has the test-target property will be carried out from among the plurality of samples when it is determined that there is the possibility of a determination of a false positive; and a test result determiner configured to determine whether or not each of the plurality of samples has the test-target property according to test results of the additional test-target samples.

The determiner may estimate a number of possible positive samples among the plurality of samples according to the test values of the plurality of pools, and determine whether or not there is the possibility of a determination of a false positive according to the estimated number of possible positive samples.

The determiner may determine that there is the possibility of a determination of a false positive when a maximum and minimum of the estimated number of possible positive samples differ from each other.

The additional sample selector may select the minimum number of additional test-target samples necessary to calculate test results of possible positive samples, which are included in each of pools whose test values are determined to be positive, other than the selected minimum number of additional test-target samples from among the possible positive samples.

The additional sample selector may sequentially select the additional test-target samples from the positively-determined pools beginning with a positively-determined pool including a minimum number of possible positive samples.

The test result determiner may determine whether or not possible positive samples included in each of the positively-determined pools other than a selected minimum number of additional test-target samples have the test-target property using a test value of the pool and test values of additional test-target samples included in the pool.

According to another aspect of the present disclosure, there is provided a biological sample analysis method for determining whether or not each of a plurality of biological samples constituting an n×m matrix has a test-target property using the plurality of biological samples and a plurality of pools generated by pooling samples of each row or column in the matrix, the method including: determining, by a determiner, whether or not there is a possibility of a determination of a false positive according to test values for the test-target property of the plurality of pools; selecting, by an additional sample selector, a minimum number of additional test-target samples on which an individual test of whether or not a sample has the test-target property will be carried out from among the plurality of samples when it is determined that there is the possibility of a determination of a false positive; and determining, by a test result determiner, whether or not each of the plurality of samples has the test-target property according to test results of the additional test-target samples.

The determining of whether or not there is the possibility of a determination of a false positive may include estimating a number of possible positive samples among the plurality of samples according to the test values of the plurality of pools, and determining whether or not there is the possibility of a determination of a false positive according to the estimated number of possible positive samples.

The determining of whether or not there is the possibility of a determination of a false positive may include determining that there is the possibility of a determination of a false positive when a maximum and minimum of the estimated number of possible positive samples differ from each other.

The selecting of the minimum number of additional test-target samples may include selecting the minimum number of additional test-target samples necessary to calculate test results of possible positive samples, which are included in each of pools whose test values are determined to be positive, other than the selected minimum number of additional test-target samples from among the possible positive samples.

The selecting of the minimum number of additional test-target samples may include sequentially selecting the additional test-target samples from the positively-determined pools beginning with a positively-determined pool including a minimum number of possible positive samples.

The determining of whether or not each of the plurality of samples has the test-target property may include determining whether or not possible positive samples included in each of the positively-determined pools other than a selected minimum number of additional test-target samples have the test-target property using a test value of the pool and test values of additional test-target samples included in the pool.

BRIEF DESCRIPTION OF THE DRAWINGS

The above and other objects, features, and advantages of the present disclosure will become more apparent to those of ordinary skill in the art by describing in detail exemplary embodiments thereof with reference to the accompanying drawings, in which:

FIG. 6 shows an algorithm for selecting an additional test-target sample according to an exemplary embodiment of the present disclosure;

FIG. 8 shows an algorithm for determining a test result of each sample based on additional test results according to an exemplary embodiment of the present disclosure;

DETAILED DESCRIPTION OF EXEMPLARY EMBODIMENTS

Hereinafter, exemplary embodiments of the present disclosure will be described in more detail with reference to the accompanying drawings. However, the present disclosure may be embedded in many different forms and should not be construed as limited to the embodiments set forth herein.

In the description of the present disclosure, when it is determined that a detailed description of related art of the present disclosure unnecessarily obscure the gist of the present disclosure, the detailed description will be omitted. Terms used in this specification are defined in consideration of functions in the present disclosure so that they may vary according to a user's and an operator's intentions or practices. Therefore, the definitions thereof should be construed based on the content throughout the specification.

The technical idea of the present disclosure is determined by the claims, and the exemplary embodiments are provided so that the technical idea of the present disclosure will be efficiently explained to those of ordinary skill in the art to which the present disclosure pertains.

A biological sample analysis system 100 according to an exemplary embodiment of the present disclosure is intended to determine whether or not each of a plurality of biological samples has a specific biological property (i.e., whether or not each of the biological samples shows a positive reaction to the specific property). Specifically, the biological sample analysis system 100 determines whether or not each of a plurality of biological samples constituting an n×m matrix has a test-target property using the plurality of biological samples and a plurality of pools generated by pooling samples of each row or column in the matrix.

Figure 1:
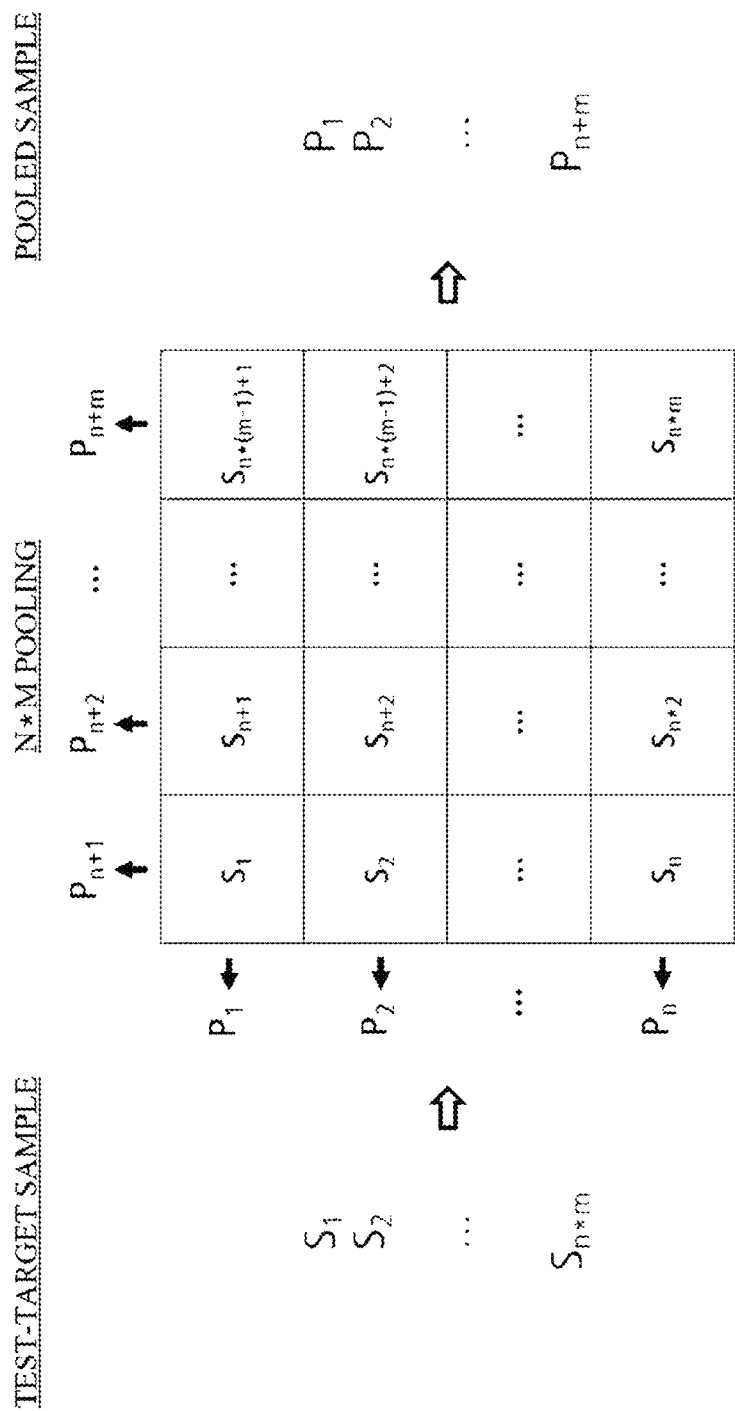
FIG. 1 is a diagram illustrating a sample pooling process according to an exemplary embodiment of the present disclosure.

Prior to description of components of the biological sample analysis system 100, a process of configuring pools with test-target samples is described with reference to FIG. 1. First, x (x=n×m) test-target samples S1, S2, . . . , and Sn×m are arranged in an n×m matrix. Here, n may be equal to or different from m, but n×m is equal to x. Also, x is equal to or greater than 2. As samples for testing whether or not they have a specific biological property, the test-target samples may be tissue, body fluid, etc. of all creatures including human.

After the matrix is generated as described above, the x test-target samples arranged in the matrix are pooled in k (=n+m) pools. At this time, samples of each row or column in the matrix are pooled in the same pool. For example, in an exemplary embodiment shown in the drawing, samples constituting a first row of the matrix are pooled in a pool $P_1$, and samples constituting a first column of the matrix are pooled in a pool $P_{n+1}$. Through this process, k pools $P_1$, $P_2$, . . . , and $P_{n+m}$ are generated.

Next, tests of the k pools in which samples are pooled are carried out to measure signals indicating the specific property to be tested. In exemplary embodiments of the present disclosure, a specific property may be a genetic marker such as a single nucleotide polymorphism (SNP), a specific genotype in a genetic marker, and a biological property such as a specific disease. In the test, the intensity of a signal denoting whether or not samples have a specific property is approximately proportional to the number of samples having the specific property in a pool. For example, when two samples have the specific property in a pool, the signal intensity resulting from the test may be about double the signal intensity of a case where one sample has the specific property in a pool. When a signal intensity measured from a specific pool is high enough to determine that one or more samples in the pool have a specific property, it is possible to say that the pool is positive to the specific property.

For example, it is assumed that the test is intended to examine whether or not samples have a specific SNP. In this case, any one of AA that is a reference genotype, AB that is a heterozygous variant genotype, and BB that is a homozygous variant genotype may be present at the corresponding variant position of a gene included in the samples. For convenience of understanding, the case of a diploid is exemplified, but the present disclosure is not limited to this case. Also, next generation sequencing (NGS) may be used as a method of measuring a signal indicating a variant genotype. NGS generates a large number of reads, which are sequence fragments of a uniform length, from a genomic area to be a target. The reads generated in this way are mapped to a reference sequence, and a sequence of a specific area is rearranged based on sequence information on reads mapped to the specific area.

In the above example, a genotype at a specific position of a test-target sample may be inferred from allele frequencies at the corresponding positions in reads mapped to an area including the specific position. For example, in the case of AB that is a heterozygous genotype, allele frequencies of A and B may be observed to be about ½ and ½, respectively. Also, when a sample having a genotype of AB and a sample having a genotype of BB are pooled, allele frequencies of A and B may be observed to be about ¼ and ¾, respectively. Therefore, to examine whether samples have a specific SNP using NGS, the allele frequency of an allele B present in the variant genotypes AB and BB may be measured based on mapped reads.

Meanwhile, when allele frequencies are calculated based on mapped reads using NGS, if the genotype of a diploidic sample is AB, the allele frequency of an alternative allele B may not be observed to be ½ or 1 at all times. This may be caused by errors such as a sequencing error or a mapping error. Therefore, in consideration of such an error, it is possible to make it a rule to allocate test result values after determining a genotype as AB when an allele frequency is observed to be between 0.4 and 0.6 and as BB when the allele frequency is observed to be 0.8 or more. Alternatively, as another method for determining the genotype of a sample based on mapped reads, a statistical algorithm for calculating a likelihood or probability of a genotype, such as an SNVer algorithm (Wei et al., SNVer: a statistical tool for variant calling in analysis of pooled or individual next-generation sequencing data, Nucleic Acids Res. 39(19), 2011) may be used. The test value of each pool may also be determined using the rule or algorithm in consideration of the number of pooled samples. However, the rule or algorithm is merely a means for implementing the present disclosure, and the present disclosure is not limited thereto.

In order to readily apply NGS to the present disclosure, it is necessary to satisfy a condition that sequencing reads of samples pooled in each pool are approximately equally distributed in the sequencing result of the pool. For example, when four pooled samples have genotypes of AA, AB, AB, and AA, respectively, the allele frequency of the alternative allele B is necessary to be observed as ⅖ in the corresponding pool.

Figure 2:
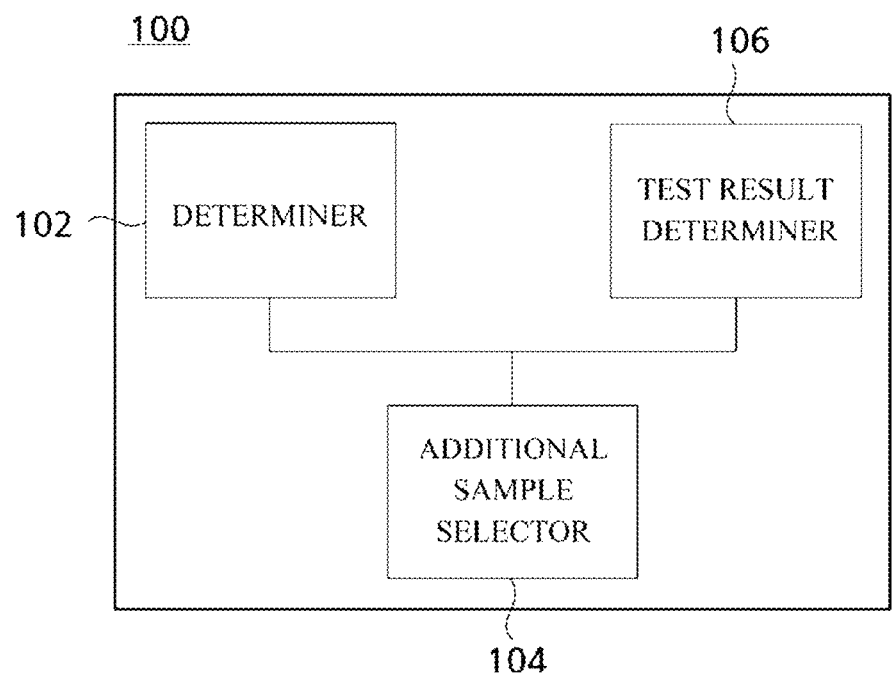
FIG. 2 is a block diagram of a biological sample analysis system according to an exemplary embodiment of the present disclosure.

FIG. 2 is a block diagram of a biological sample analysis system according to an exemplary embodiment of the present disclosure. As shown in the drawing, the biological sample analysis system 100 according to an exemplary embodiment of the present disclosure includes a determiner 102, an additional sample selector 104, and a test result determiner 106.

The determiner 102 determines whether or not there is the possibility of a determination of a false positive according to test values for the test-target property of the plurality of pools generated from the matrix.

The additional sample selector 104 selects a minimum number of additional test-target samples on which additional individual tests will be carried out from among the plurality of test-target samples when the determiner 102 determines that there is the possibility of a determination of a false positive.

The test result determiner 106 determines whether or not each of the plurality of samples has the test-target property according to the test values of the plurality of pools and test results of the additional test-target samples.

Each of the components of the biological sample analysis system 100 configured as described above according to an exemplary embodiment of the present disclosure will be described in detail below.

Determination of Whether or not there is Possibility of Determination of False Positive As described above, the determiner 102 determines whether or not there is the possibility of a determination of a false positive according to test values for the test-target property of the plurality of pools generated from the matrix. When it is determined that there is the possibility of a determination of a false positive, individual tests are carried out on some or all samples of positive pools.

Figure 3:
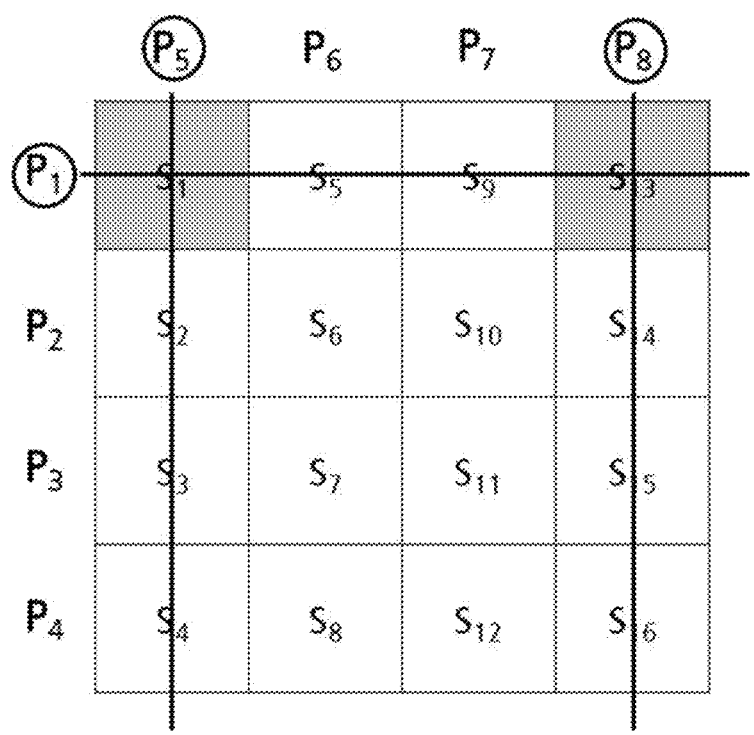
FIGS. 3 and 4 are diagrams illustrating a method of estimating a positive sample according to an exemplary embodiment of the present disclosure.

In an n×m pooling method according to an exemplary embodiment of the present disclosure, a sample corresponding to a point where a positive row pool and a positive column pool intersect in an n×m matrix is determined to be positive. For example, as shown in FIG. 3, when the pools $P_1$, $P_5$, and $P_8$ are positive, samples $S_1$ and $S_{13}$ are determined to be positive. If the possibility of positive samples being present among samples is low, this method is good enough to determine a positive sample.

Figure 4:
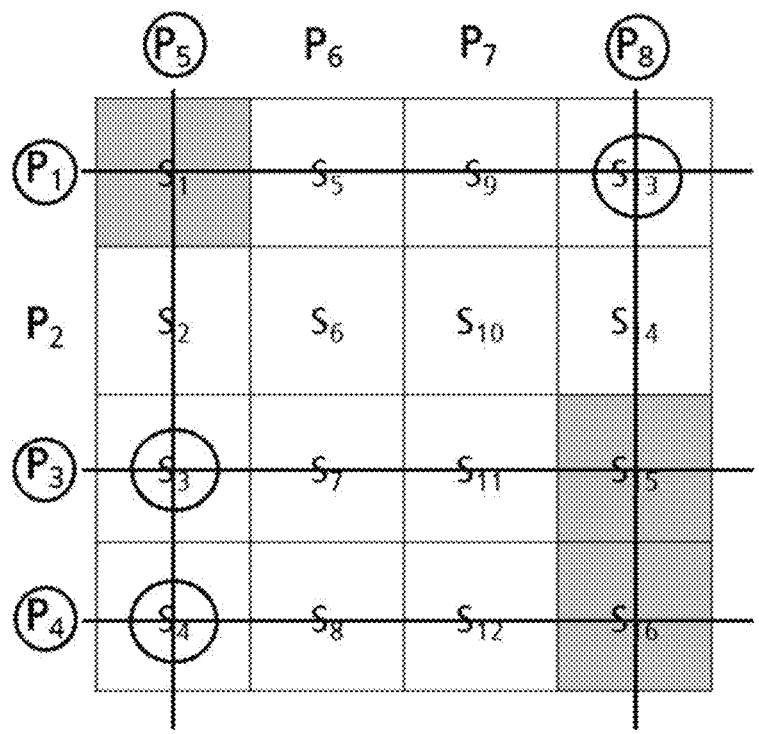

Meanwhile, when $S_1$, $S_{15}$, and $S_{16}$ are actually positive as shown in FIG. 4, pools $P_1$, $P_3$, $P_4$, $P_5$, and $P_8$ are observed to be positive. However, according to the above-described method, samples $S_1$, $S_3$, $S_4$, $S_{13}$, $S_{15}$, and $S_{16}$ are determined to be positive, and $S_3$, $S_4$, and $S_{13}$ among them are incorrectly determined to be positive (i.e., false-positive samples). Therefore, it is necessary to determine whether or not there is the possibility of a determination of a false positive according to test results of respective pools.

In exemplary embodiments of the present disclosure, the determiner 102 estimates the number of possible positive samples among the plurality of samples according to the test values of the plurality of pools, and determines whether or not there is the possibility of a determination of a false positive according to the estimated number of possible positive samples. First, the determiner 102 allocates a value p(k) to a pool k ($1 \le k \le n+m$) based on a measured value of each pool as follows:

$$p(k) = \begin{cases} 1, & \text{if pool } k \text{ is positive} \\ 0, & \text{if pool } k \text{ is negative} \end{cases} \text{ where } 1 \le k \le n+m.$$

After p(k) of each pool is determined, the determiner 102 generates a new n×m matrix M based on the allocated values as follows:

$$M(i, j) = \begin{cases} 1, & \text{if } p(i) = 1 \text{ and } p(n+j) = 1 \\ 0, & \text{otherwise} \end{cases}$$

where i=row index ($1 < i \le n$), j=column index ($1 \le j \le m$)

Subsequently, the determiner 102 calculates a minimum minPositive and a maximum maxPositive of the number of possible positive samples using the matrix M. Here, min-Positive and maxPositive respectively denote the maximum and minimum of the number of possible positive samples that may be estimated according to test results of the pools.

$$\text{minPositive} = \text{MAX}\left(\sum_{k=1}^{n} p(k), \sum_{k=n+1}^{n+m} p(k)\right)$$

$$\text{maxPositive} = \sum_{i=1}^{n} \sum_{j=1}^{m} M(i, j)$$

The determiner 102 determines whether or not there is the possibility of a determination of a false positive using the calculated maximum maxPositive and the calculated minimum minPositive. Specifically, when maxPositive differs from minPositive, the determiner 102 determines that there is the possibility of a determination of a false positive.

Figure 5:
FIG. 5 is a diagram illustrating a process of generating a matrix and calculating a minPositive and a maxPositive from the matrix in the exemplary embodiment shown in FIG. 4.

FIG. 5 is a diagram showing the matrix M and minPositive and maxPositive calculated from the matrix M in the exemplary embodiment shown in FIG. 4, that is, a case where test results of $P_1$, $P_3$, $P_4$, $P_5$, and $P_8$ are positive. As shown in the drawing, in this exemplary embodiment, minPositive of 3 differs from maxPositive of 6. Therefore, there is the possibility of a determination of a false positive, and additional individual tests are necessary for some samples.

Selection of Minimum Samples for Additional Individual Tests

As described above, when the determiner 102 determines that there is the possibility of a determination of a false positive, the additional sample selector 104 selects a minimum number of additional test-target samples on which additional individual tests will be carried out from among the plurality of test-target samples.

In exemplary embodiments of the present disclosure, the additional sample selector 104 is configured not to carry out individual tests on all samples that are likely to be positive but to carry out additional individual tests on as a small number of samples as possible. This is because an increase in the number of samples to be subjected to additional individual tests leads to an increase in cost and time for tests. However, this is based on the premise that the intensity of a signal denoting whether or not a sample has a specific property (i.e., the signal intensity of each pool) is approximately proportional to the number of samples having the specific property in a pool. When it is possible to know whether or not a positive sample is present in a pool from a test result, but it is difficult to expect that the intensity of the signal will be approximately proportional to the number of positive samples, it is necessary to carry out additional individual tests on all samples in a positive pool. However, even in this case, it is determined whether or not there is the possibility of a determination of a false positive so that additional tests are carried out only when there is the possibility of a determination of a false positive. Therefore, there are advantages in terms of cost and time compared to related art in which additional tests are carried out on all possible positive samples at all times.

When it is determined that there is the possibility of a determination of a false positive, the additional sample selector 104 selects a minimum number of samples on which additional individual tests will be carried out. The additional individual tests may be the test carried out on the pools, or another test in which another technology for measuring a specific property, which is a test target, is used.

The additional sample selector 104 is configured to select a minimum number of additional test-target samples necessary to calculate test results of possible positive samples, which are included in each of pools determined to be positive (positively-determined pools) according to their test values, other than the selected minimum number of additional test-target samples from among the possible positive samples. A detailed algorithm for selecting additional test-target samples is shown in FIG. 6.

Figure 7:
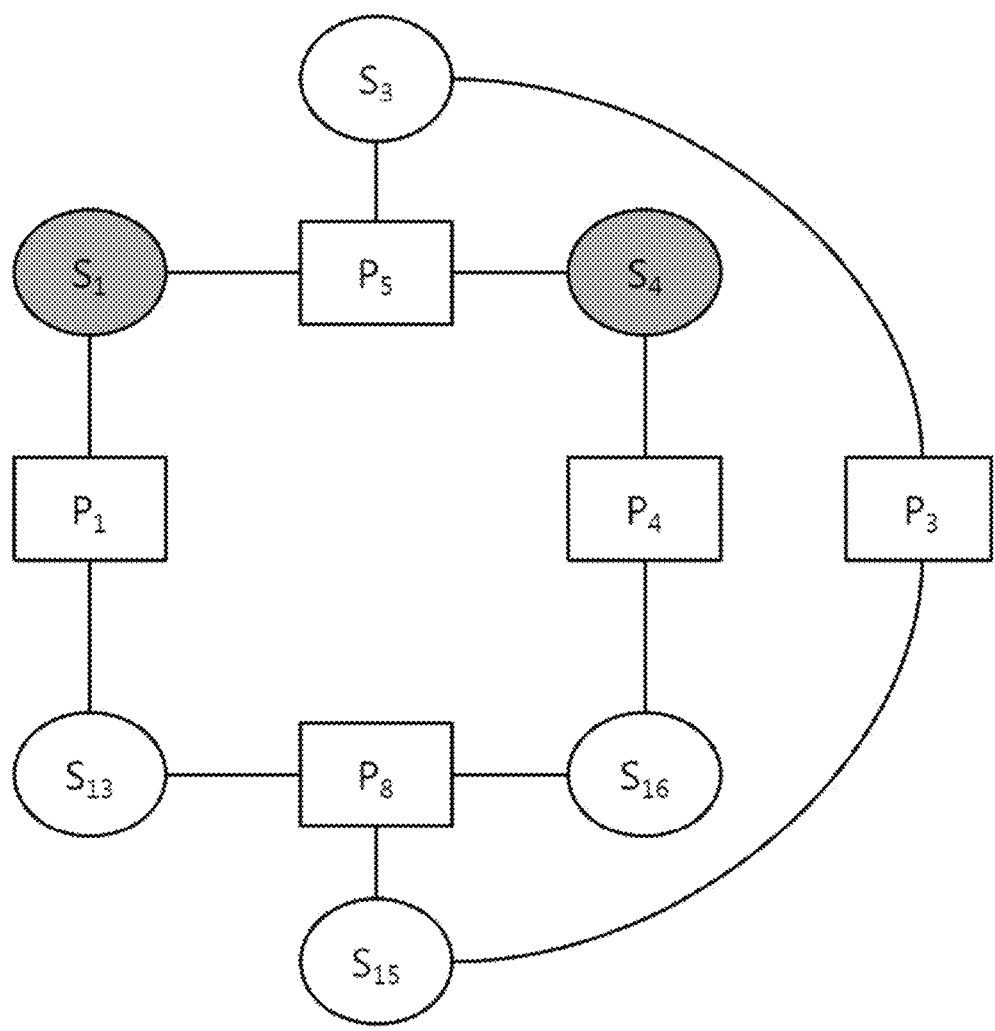
FIG. 7 is a diagram illustrating a graph derived from the exemplary embodiment shown in FIG. 4.

Using the example shown in FIG. 4, the algorithm shown in FIG. 6 is described as follows. First, the additional sample selector 104 generates a graph G that has the pools $P_1$, $P_3$, $P_4$, $P_5$, and $P_8$ determined to be positive and the possible positive samples $S_1$, $S_3$, $S_4$, $S_{13}$, $S_{15}$, and $S_{16}$ inferred from the positively-determined pools as vertexes and has lines connecting the positively-determined pools with the possible positive samples as edges. The graph G generated in this way is shown in FIG. 7.

After the graph G is generated, the additional sample selector 104 selects a pool having a minimum number of neighbors, that is, a pool including a minimum number of possible positive samples, from among the pools included in the graph, and create a set D consisting of neighbors of the selected pool. In an exemplary embodiment shown in the drawing, pools having a minimum number of neighbors are $P_1$, $P_3$, and $P_4$ having two neighbors, and thus one of them, for example, $P_1$, is selected. Then, it is satisfied that D={$S_1$, $S_{13}$}.

Subsequently, the additional sample selector 104 removes one sample from the set D and checks whether or not the set D is empty. If the set D is not empty even after the one sample is removed, the additional sample selector 104 selects the removed sample as an additional test-target sample. For example, since $S_{13}$ remains in the set D even after $S_1$ is removed from the set D, the additional sample selector 104 selects $S_1$ as an additional test-target sample and removes it from the graph G. If the set D is empty after one sample is removed, the additional sample selector 104 removes the removed sample from the graph G without selecting it as an additional test-target sample. For example, after $S_1$ is selected, only $S_{13}$ remains in the set D, and when $S_{13}$ is removed from the set D, the set D becomes an empty set. Therefore, $S_{13}$ is not selected as an additional test-target sample. These processes are repeated until the set D becomes empty, and thereafter repeated for another pool that has not been selected. These processes are sequentially summarized as follows:

1. Select $P_1$
2. Select $S_1$ for individual test
3. Skip $S_{13}$
4. Select $P_4$
5. Select $S_4$ for individual test
6. Skip $S_{16}$
7. Select $P_5$
8. Skip $S_3$
9. Select $P_8$
10. Skip $S_{15}$
11. Select $P_3$
12. Done In other words, through the above processes, $S_1$ and $S_4$ are selected as additional test-target samples from among the six possible positive samples (shown in grey in the drawing).

Determination of Test Result of Individual Sample

After additional test-target samples are selected through the above-described processes and additional tests of the selected samples are finished, the test result determiner 106 determines whether or not each of the plurality of samples has the test-target property according to the test values of the plurality of pools and the test values of the additional test-target samples.

As described above, in order for the test result determiner 106 to determine test results, when a pool is tested, the intensity of a signal measured for a specific property is necessary to be approximately proportional to the number of samples having the property. A test result value of a pool is necessary to be the sum of test result values of positive samples included in the pool. Using these characteristics, the test result determiner 106 determines a test result of each sample. In other words, the test result determiner 106 is configured to determine whether or not possible positive samples other than additional test-target samples included in each of the positively-determined pools have the test-target property using the test value of the pool and the test values of the additional test-target samples. A detailed algorithm for the test result determiner 106 to determine a result value is shown in FIG. 8.

Using the example shown in FIG. 4, the algorithm shown in FIG. 6 is described as follows. Based on an allele frequency of an alternative allele B, it is possible to allocate a test result value (valS in FIG. 8) to each sample, such as 0 in the case of the reference genotype AA, 1 in the case of the heterozygous variant genotype AB, and 2 in the case of the homozygous variant genotype BB. In this case, a test result value (vale in FIG. 8) of a positive pool is the sum of test result values of positive samples in the corresponding pool. For example, the test value, that is, signal intensity, of $P_5$ is the sum of test values of $S_1$, $S_3$ and $S_4$ (valP[5]=valS[1]+valS[3]+valS[4]). Accordingly, from the test values of $S_1$ and $S_4$ obtained through the additional individual tests and the test value of $P_5$ obtained through the initial test, the test result determiner 106 may calculate the test value of $S_3$. By repeating this process, it is possible to calculate the test values of all the samples.

Figure 9:
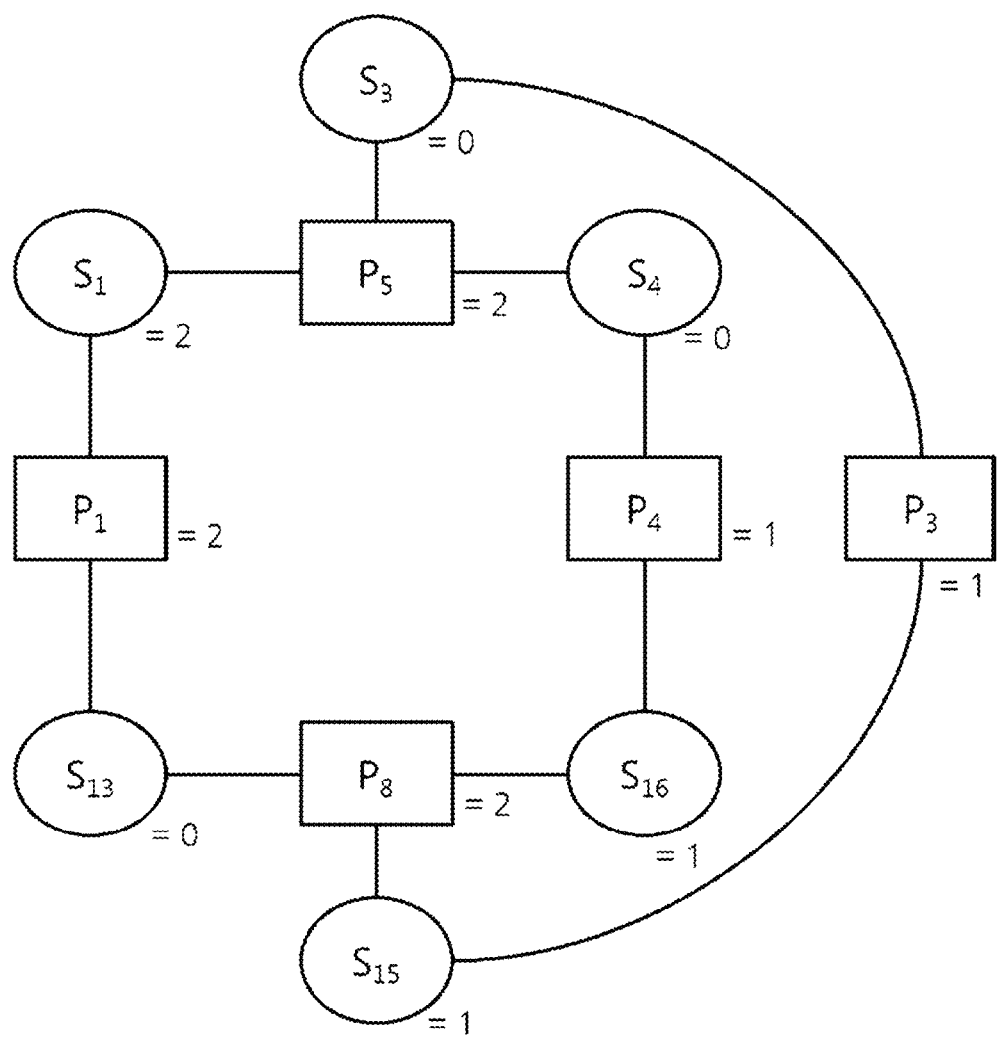
FIG. 9 is a diagram illustrating a process of estimating a test result of each sample in the graph shown in FIG. 7.

FIG. 9 shows an example in which the test values of possible positive samples are calculated when the test values of $P_1$, $P_3$, $P_4$, $P_5$, and $P_8$ are 2, 1, 1, 2, and 2, respectively and the test values of the additional test-target samples $S_1$ and $S_4$ are 2 and 0, respectively. As shown in the drawing, the test value of each possible positive sample may be calculated as follows:

$$valS[S_3]=valP[P_5]-valS[S_1]-valS[S_4]=2-2-0=0$$

$$valS[S_{13}]=valP[P_1]-valS[S_1]=2-2=0$$

$$valS[S_{16}]=valP[P_4]-valS[S_4]=1-0=1$$

$$valS[S_{15}]=valP[P_8]-valS[S_{13}]-valS[S_{16}]=2-0-1=1.$$

As described above, according to exemplary embodiment of the present disclosure, x individual tests are not carried out on x samples, but only k tests are carried out on k pools through pooling of samples, and based on results of the k tests, it is possible to estimate the individual test results of the x samples. In other words, exemplary embodiments of the present disclosure make it possible to estimate the rest results of all of the x samples from the k tests, thus reducing cost and time for (x−k) tests. Even if additional individual tests are necessary for q samples after the k tests because a sample determined to be positive has a possibility of being determined to be false positive, it is still possible to reduce cost and time for (x−k−q) tests.

Figure 10:
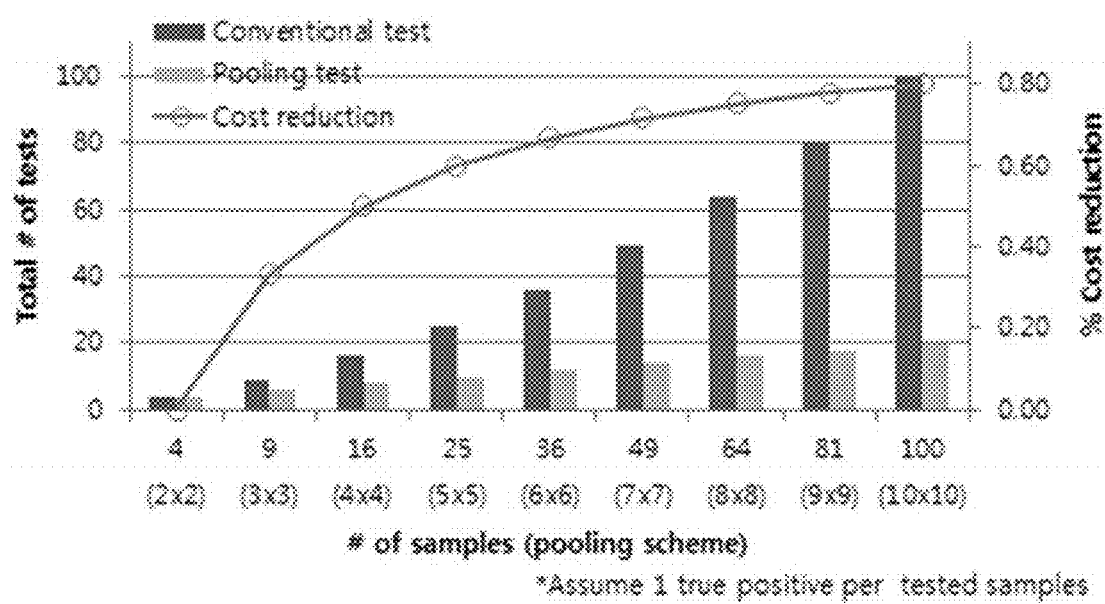
FIG. 10 shows a graph comparatively illustrating a total number of tests upon carrying out sample pooling tests according to exemplary embodiments of the present disclosure and a total number of tests upon carrying out individual tests on samples.

FIG. 10 shows a graph comparatively illustrating a total number of tests upon carrying out sample pooling tests according to exemplary embodiments of the present disclosure and a total number of tests upon carrying out individual tests on samples. In the shown graph, the horizontal axis denotes the number of samples, bar graphs on the left side denote the number of individual tests carried out on respective samples, bar graphs on the right side denote the number of sampling pooling tests according to exemplary embodiments of the present disclosure, and the line graph denotes a cost reduction effect according to the difference in the number of tests between the two cases. For example, when 16 samples are tested, 16 tests are carried out according to the existing method, whereas only eight tests are carried out using a 4×4 sample pooling method. Therefore, it is possible to expect a cost reduction effect of a maximum of 50%.

According to the sample pooling method, a test is carried out on pooled samples, and an additional individual test is carried out on a sample having a possibility of being determined to be false positive. Therefore, in the worst case, more tests may be carried out compared to an existing method. FIG. 11 shows graphs for comparing total numbers of tests according to a change in the number of positive samples present among test-target samples. In the shown graphs, the horizontal axes denote the number of positive samples present among test-target samples, the dotted lines denote the number of tests in the case of using an existing method of carrying out an individual test on each sample (conventional test without pooling), the dark grey lines denote the number of tests in the case of using the sample pooling method and carrying out individual tests on all the corresponding samples when there is the possibility of a determination of a false positive (n×n pooling test), and light grey lines denote the number of tests in the case of using a method of selecting a minimum number of samples on which individual tests will be carried from among samples having a possibility of being determined to be false positive together with the sample pooling method (n×n pooling test+Min. # of sample selection).

Figure 11A:
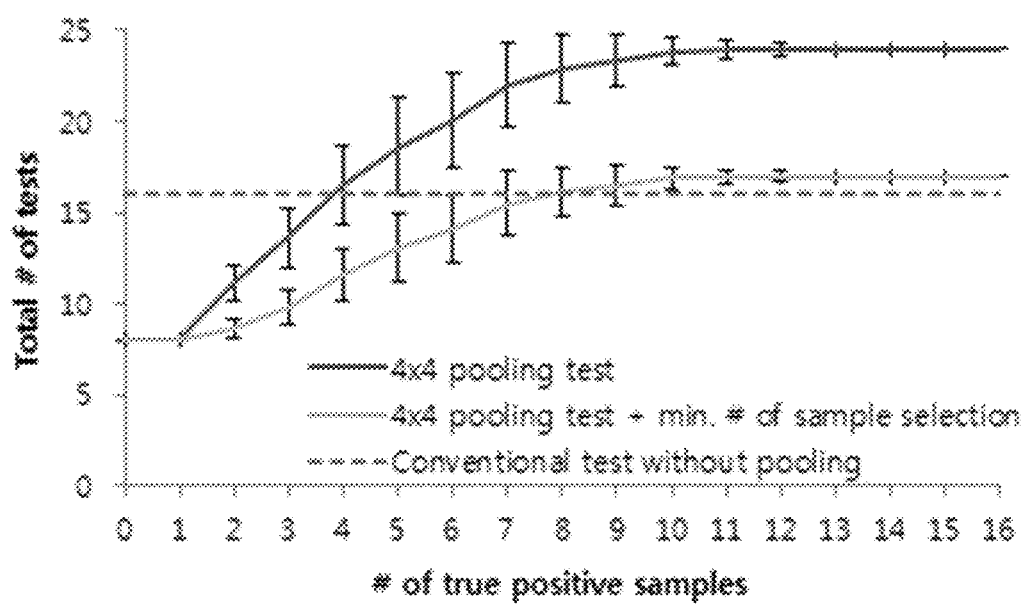
FIG. 11(A) illustrates testing samples using one sample pooling method.
Figure 11B:
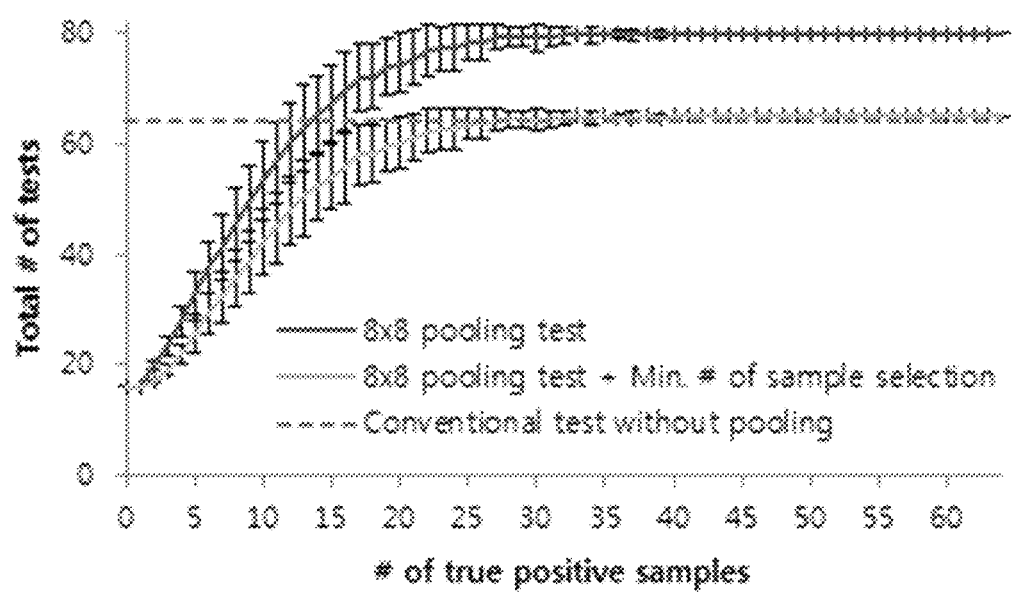
FIG. 11(B) illustrates testing samples using another sample pooling method.

In addition, the graph of FIG. 11(A) illustrates the case of testing 16 samples using the 4×4 sample pooling method, and the graph of FIG. 11(B) illustrates the case of testing 64 samples using an 8×8 sample pooling method. For comparison, 100 test cases that randomly generated positive samples among test-target samples were created per a number of positive samples, and the number of tests for each test case was calculated. In the drawing, the average number of tests and the standard deviation of the average number (shown in "I" shape in the graphs) are shown together.

First, referring to FIG. 11(A), it is possible to see that, even when additional tests are carried out on all samples having a possibility of being determined to be false positive, a smaller number of tests are carried out compared to the number of tests according to the existing method (dotted line) until the number of positive samples present among 16 samples becomes three. For example, in the case of a disease test, when the incidence of the corresponding disease is about 3/16 (=0.188), it is generally possible to expect that three samples among 16 samples will be positive. However, this is a very high incidence, and an incidence is generally lower than the value. Therefore, in general, the sample pooling method may reduce cost for tests. Also, it is possible to see that the algorithm for selecting a minimum number of additional test-target samples according to exemplary embodiments of the present disclosure reduces cost by about 14% to about 30% due to a reduction in the number of tests compared to the case of not using the algorithm.

In addition, referring to FIG. 11(B), it is possible to see that, in the worst case where all the 64 samples are positive, 80 tests are carried out when the algorithm according to exemplary embodiments of the present disclosure is not used, but only 65 tests are carried out when the algorithm is used. In other words, even in the worst case, exemplary embodiments of the present disclosure involve only one more test than the existing method.

As a result, the results of FIG. 11 show that the sample pooling method proposed in exemplary embodiments of the present disclosure has a cost reduction effect in spite of an increase in the number of positive samples in a general case, and involves a slight increase in the number of tests to be additionally carried out even in the worst case compared to the existing test method.

Figure 12:
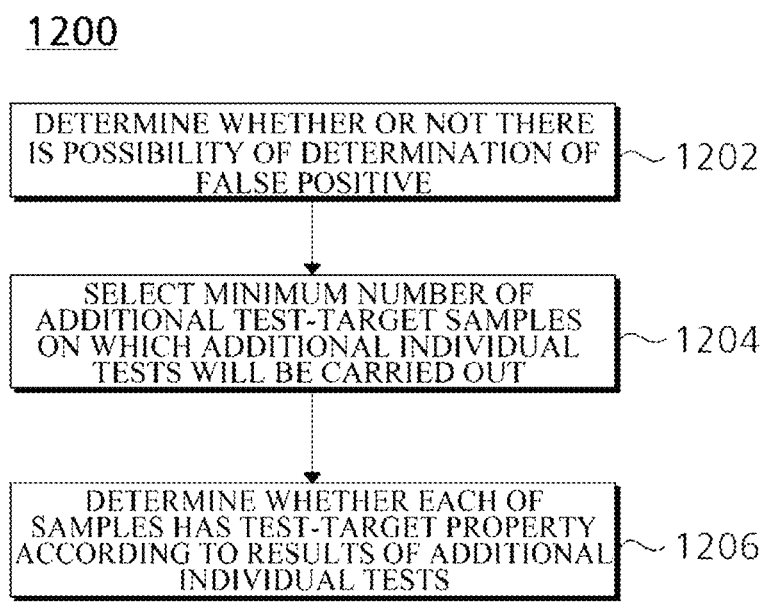
FIG. 12 is a flowchart illustrating a biological sample analysis method according to an exemplary embodiment of the present disclosure.

FIG. 12 is a flowchart illustrating a biological sample analysis method according to an exemplary embodiment of the present disclosure. As described above, a biological sample analysis method 1200 according to an exemplary embodiment of the present disclosure is intended to determine whether or not each of a plurality of biological samples constituting an n×m matrix has a test-target property using the plurality of biological samples and a plurality of pools generated by pooling samples of each row or column in the matrix.

In step 1202, the determiner 102 determines whether or not there is the possibility of a determination of a false positive according to test values for the test-target property of the plurality of pools.

In step 1204, the additional sample selector 104 selects a minimum number of additional test-target samples on which an individual test of whether or not a sample has the test-target property will be carried out from among the plurality of samples when it is determined in step 1202 that there is the possibility of a determination of a false positive.

In step 1206, the test result determiner 106 determines whether or not each of the plurality of samples has the test-target property according to test results of the additional test-target samples.

Meanwhile, exemplary embodiments of the present disclosure may include a computer-readable recording medium including a program for performing the methods described herein on a computer. The computer-readable recording medium may separately include program commands, local data files, local data structures, etc. or include a combination of them. The medium may be specially designed and configured for the present disclosure, or known and available to those of ordinary skill in the field of computer software. Examples of the computer-readable recording medium include magnetic media, such as a hard disk, a floppy disk, and a magnetic tape, optical recording media, such as a CD-ROM and a DVD, magneto-optical media, such as an optical disk, and hardware devices, such as a ROM, a RAM, and a flash memory, specially configured to store and execute program commands. Examples of the program commands may include high-level language codes executable by a computer using an interpreter, etc. as well as machine language codes made by compilers.

According to exemplary embodiments of the present disclosure, pools are generated by pooling one or more samples to be tested, and then an individual test result of each sample is calculated based on test results of the pools. Therefore, in comparison with a case of individually carrying out tests on all samples, the number of tests is reduced, and it is possible to obtain the same result.

In addition, according to exemplary embodiment of the present disclosure, it is possible to minimize the number of samples to be additionally subjected to individual tests even when a test result based on the sample pooling method indicates that there is the possibility of a determination of a false positive. Therefore, it is possible to obtain accurate test results in which there is no possibility of a determination of a false positive even while minimizing time and cost necessary for tests.

It will be apparent to those skilled in the art that various modifications can be made to the above-described exemplary embodiments of the present disclosure without departing from the spirit or scope of the present disclosure. Thus, it is intended that the present disclosure covers all such modifications provided they come within the scope of the appended claims and their equivalents.

What is claimed is:

1. A biological sample analysis system for determining a test-target property of a biological sample, the system comprising at least one processor to implement:
   a sample selector configured to select, among a plurality of biological samples constituting an n×m matrix, a plurality of pools, generated from the n×m matrix, on a per-row or a per-column basis, wherein biological samples of each row or column in the n×m matrix are pooled in the same pool;
   a tester configured to obtain test values, for the test-target property, for the plurality of pools;
   a determiner configured to receive, from the tester, the test values, for the test-target property, for the plurality of pools, and determine a possibility of a false positive according to the test values, for the test-target property, for the plurality of pools;
   a second sample selector configured to respond to the possibility of the false positive by selecting at least one biological sample from biological samples included in each of pools determined to be positive according to the test values; and
   a test result determiner configured to receive, from the tester, test values obtained from each individual test, for the test-target property, of the at least one biological sample selected by the second sample selector, and make a determination as to whether each of the plurality of biological samples constituting the n×m matrix has the test-target property according to the test values obtained from each individual test of the selected at least one biological sample.

2. The biological sample analysis system of claim 1, wherein the determiner is further configured to determine an estimated number indicating possible positive samples of the plurality of biological samples, according to the test values of the plurality of pools, and to determine the possibility of the false positive based on the estimated number.

3. The biological sample analysis system of claim 2, wherein the determiner determines the possibility of the false positive when a maximum and a minimum of the estimated number differ from each other.

4. The biological sample analysis system of claim 1, wherein:
   ones of the plurality of biological samples having a positive indication of the test-target property define positively-determined biological samples; and
   the second sample selector selects a minimum number of the at least one biological sample among positively-determined biological samples included in each of the pools determined to be positive, the minimum number being necessary for determining test results of biological samples, other than the positively-determined biological samples, included in each of the pools determined to be positive.

5. The biological sample analysis system of claim 4, wherein:
ones of the plurality of pools having at least one of the positively-determined biological samples define one or more positively-determined pools; and
the second sample selector sequentially selects the at least one biological sample from the one or more positively-determined pools beginning with the one of the one or more positively-determined pools having a minimum number of positively-determined biological samples.

6. The biological sample analysis system of claim 4, wherein:
ones of the plurality of pools having at least one of the positively-determined biological samples define one or more positively-determined pools; and
the test result determiner determines whether the positively-determined biological samples included in each of the one or more positively-determined pools, other than the selected minimum number of the at least one biological sample, have the test-target property, using a test value of the pool and test values of the selected minimum number of the at least one biological sample included in the pool.

7. A biological sample analysis method for determining a test-target property of a biological sample, the method comprising:
selecting, among a plurality of biological samples constituting an n×m matrix, a plurality of pools, generated from the n×m matrix, on a per-row or a per-column basis, wherein biological samples of each row or column in the n×m matrix are pooled in the same pool;
obtaining, from a tester, test values, for the test-target property, for the plurality of pools;
receiving, from the tester, the test values, for the test-target property, for the plurality of pools, and determining a possibility of a false positive according to the test values, for the test-target property, for the plurality of pools;
responding to the possibility of the false positive by selecting at least one biological sample from biological samples included in each of pools determined to be positive according to the test values; and
receiving, from the tester, test values obtained from each individual test, for the test-target property, of the selected at least one biological sample, and making a determination as to whether each of the plurality of biological samples constituting the n×m matrix has the test-target property according to the test values obtained from each individual test of the selected at least one biological sample.

8. The biological sample analysis method of claim 7, wherein the determining of the possibility of the false positive includes determining an estimated number indicating possible positive samples of the plurality of biological samples, according to the test values of the plurality of pools, and determining the possibility of the false positive based on the estimated number.

9. The biological sample analysis method of claim 8, wherein the determining of the possibility of the false positive is made when a maximum and a minimum of the estimated number differ from each other.

10. The biological sample analysis method of claim 7, wherein:
ones of the plurality of biological samples having a positive indication of the test-target property define positively-determined biological samples; and
the selecting the at least one biological sample comprises selecting a minimum number of the at least one biological sample among positively-determined biological samples included in each of the pools determined to be positive, the minimum number being necessary for determining test results of biological samples, other than the positively-determined biological samples, included in each of the pools determined to be positive.

11. The biological sample analysis method of claim 10, wherein:
ones of the plurality of pools having at least one of the positively-determined biological samples define one or more positively-determined pools; and
the selecting of the minimum number of the at least one biological sample comprises sequentially selecting the at least one biological sample from the one or more positively-determined pools beginning with the one of the one or more positively-determined pools having a minimum number of positively-determined biological samples.

12. The biological sample analysis method of claim 10, wherein:
ones of the plurality of pools having at least one of the positively-determined biological samples define one or more positively-determined pools; and
the determining of whether each of the plurality of biological samples has the test-target property includes determining whether or not positively-determined biological samples included in each of the one or more positively-determined pools, other than a selected minimum number of additional biological samples, have the test-target property, using a test value of the pool and test values of the selected minimum number of the at least one biological sample included in the pool.

* * * * *